(12) United States Patent
Colaianni

(10) Patent No.: US 6,336,905 B1
(45) Date of Patent: Jan. 8, 2002

(54) ENDOCERVICAL SAMPLING DEVICE

(76) Inventor: Rana A. Colaianni, 96 Butters Rd., Williamsport, PA (US) 17701

( * ) Notice: Subject to any disclaimer, the term of this patent is extended or adjusted under 35 U.S.C. 154(b) by 0 days.

(21) Appl. No.: 09/426,368

(22) Filed: Oct. 25, 1999

Related U.S. Application Data

(60) Provisional application No. 60/106,483, filed on Oct. 30, 1998.

(51) Int. Cl.[7] .............................................. A61B 10/00
(52) U.S. Cl. ...................................................... 600/569
(58) Field of Search ................................ 600/569, 570, 600/572

(56) References Cited

U.S. PATENT DOCUMENTS

| | | | |
|---|---|---|---|
| 4,157,709 A | * 6/1979 | Schuster et al. | ............ 600/572 |
| 4,277,537 A | 7/1981 | Suciu et al. | ................ 128/756 |
| 4,457,313 A | * 7/1984 | Alter | ............................ 600/572 |
| 5,129,402 A | * 7/1992 | Koll et al. | ................... 600/572 |
| 5,146,928 A | 9/1992 | Esser | |
| 5,173,369 A | 12/1992 | Tao | ............................. 128/756 |
| 5,456,265 A | 10/1995 | Yim | ............................. 128/756 |
| 5,792,074 A | * 8/1998 | Turkel et al. | ............... 800/569 |

OTHER PUBLICATIONS

Weitzman, GA et al 1988 Endocervical Brush Cytology—An Alternative to Endocervical Curettage Journal of Reproductive Medicine 33:677–83.

Hoffman, MS et al 1993 Evaluation of Endocervical Canal with the Endocervical Brush Obstetrics/Gynecology 82:573–7.

Cox, T. 1997 ASCCP Practice Guidelines: Endocervical Curettage. Journal of the Lower Genital Tract Disease vol. 1, Nov. 4, 1997 251–256.

* cited by examiner

Primary Examiner—Eric F. Winakur
Assistant Examiner—Pamela L. Wingood
(74) Attorney, Agent, or Firm—Webb, Ziesenheim Logsdon Orkin & Hanson, P.C.

(57) ABSTRACT

An endocervical sampling device 10 and method comprising a cytology brush 12 slidably received within a protective cylindrical sleeve 14 and having a tapered distal tip 16 protected by a penetrable seal 18.

9 Claims, 2 Drawing Sheets

ENDOCERVICAL SAMPLING DEVICE

CROSS REFERENCE TO RELATED APPLICATIONS

This application is entitled to the benefit of provisional patent application Ser. No. 60/106,483, filed Oct. 30, 1998.

BACKGROUND—FIELD OF INVENTION

This invention is directed to a medical sampling device for use with gynecological examinations, particularly to an improved method of obtaining endocervical cell and tissue samples during colposcopy.

BACKGROUND—DESCRIPTION OF PRIOR ART

The most widely used cervical cancer screening test is the well-known pap smear. When an abnormality is detected, further evaluation and follow up are warranted. The most common follow up test after an abnormal pap smear is colposcopy. Colposcopy is a visual inspection of the lower genital tract using a low power microscope. This test is limited to visualization of the surface of the uterine cervix, and cannot adequately detect problems within the endocervical canal. The incidence of cervical adenocarcinoma is increasing. It is estimated that up to 20% of cervical cancers occur within the cervical canal, and are not readily visible during colposcopy. Because of this significant limitation of colposcopy, the cells and tissues of the endocervical canal must be adequately sampled to allow for microscopic evaluation and accurate diagnosis. Appropriate endocervical sampling can present further diagnostic excisional (surgical) procedures in the majority of patients.

There are presently several commonly used methods to sample the endocervical canal. It is estimated that the total annual cost of aggresive management is almost four billion dollars in the United States alone. One method to sample the endocervical canal is the endocervical curettage. This method employs utilizing a "curette," generally a metal instrument with sharp edges which scrape the walls of the endocervical canal.

A disadvantage of the curette method is that this method generally suffers from a poor cell yield. This leads to inadequate sampling and "false negative" results, thus requiring further investigation. This includes repeat sampling or surgical intervention, such as cone biopsy or other excisional procedure. This potentially causes an increase in patient discomfort, morbidity and cost.

A second disadvantage is that upon insertion of the curette into the cervical os (opening), the curette often inadvertently scrapes or "nicks" the ectocervix, (surface of the cervix) causing a "false positive" result, necessitating further evaluation. This, again, potentially causes increased discomfort, morbidity and cost.

Another disadvantage of the curette method is patient discomfort as the specimen "scrapes" along the endocervical walls.

Another disadvantage of the curette method is cost to process the specimen. In most institutions, the specimen obtained in this manner is processed "histologically," that is, by the pathology department. In general, this cost is greater than with samples obtained with brush methods.

Another disadvantage of the curette method is the need to sterilize the instrument, increasing the potential of infection to the patient and health care workers, and adding to increased overall cost of care.

Another common method of evaluating the endocervical canal is with a standard cytology brush. While this method improves cell yield over the curette, it suffers from ease of contamination of the brush from cells or tissues at or near the canal opening, as the brush is inserted and withdrawn, causing "false positives." This "false positive" rate remains a major weakness of the brush method and potentially leads to further evaluation. This increases patient discomfort, morbidity and cost.

Another disadvantage of the standard cytology brush evaluation of the endocervical canal is lack of sterility of most commonly used cytology brushes. These are generally purchased in bulk and cannot be sterilized just prior to use during colposcopy.

Another method to sample the endocervical canal during colposcopy utilizes a cytology brush with a standard drinking straw as a protective sheath. There are several key disadvantages to this system. The first disadvantage is that the opening of a standard drinking straw does not accommodate the majority of cervical opening sizes. This is secondary to its fixed opening size, and the lack of conformity to the cervical opening. In addition, the straw is awkward to handle and manipulate, often slipping from the operators gloved fingers.

Another disadvantage is the need, in most cases, to cut and trim the straw to a length less than the cytology brush, adding extra steps to the procedure and decreasing efficiency.

Another disadvantage is that the brush often inadvertently advances forward before the operator is ready to sample, potentially causing the specimen to become contaminated with cells or tissues from the ectocervix.

Another disadvantage is the inability of the operator to determine the depth of insertion into the endocervical canal.

Another disadvantage is the inability of the operator to judge the position of the brush back in the protective sleeve prior to withdrawal.

Another disadvantage is the straw edges are sharp having the potential to cause tissue trauma or crushing artifact of the specimen.

Another endocervical brush assembly and method is disposed in U.S. Pat. No. 5,456,265 by Yim issued 10/10/95. This device suffers from several of the same shortcomings as the brush-plus-straw method. First, the opening size of the distal tip will not accommodate the majority of cervical openings. A second disadvantage is that the distal end is covered by a small cap which must be removed prior to insertion. Failure to remove this cap could potentially result in a foreign body being left in the patient. A third disadvantage is that it is difficult for the operator to determine the depth of insertion into the endocervical canal. A fourth disadvantage is that after the cap is removed, the distal brush bristles remained unprotected as insertion proceeds, risking contamination to the endocervical specimen with cells from the ectocervix. A fifth disadvantage is that this device requires bimanual operation.

With the high number of abnormal pap smears, and the high incidence of error associated with curette sampling methods, there is a need for an inexpensive, accurate, simple, safe, and effective method to collect endocervical cells.

SUMMARY

In accordance with the present invention, an endocervical sampling device comprising a cytology brush encased in a protective sleeve, and a tapered distal tip with a protective penetrable seal.

Objects and Advantages

It is a general object of the present invention to provide an endocervical sampling device which solves the technical problems long associated with endocervical sampling while overcoming the disadvantages of the prior art. Several objectives and advantages of the present invention are:

(a) To provide an inexpensive endocervical sampling device which protects the integrity of the sample by protecting the brush from contamination from tissue and cell fragments on the endocervix during insertion or withdrawal.

(b) To provide an inexpensive endocervical sampling device that accommodates the majority of cervical opening sizes, eliminating the need for multiple devices.

(c) To provide an inexpensive endocervical sampling device that provides the operator with visual confirmation of the position and depth of the brush within the endocervical canal.

(d) To provide an inexpensive endocervical sampling device for sterile, single use application to minimize the risk of infection to the patient and health care workers.

(e) To provide an inexpensive endocervical sampling device that promotes patient comfort.

(f) To provide an inexpensive endocervical sampling device that is easy to maneuver.

(g) To provide an inexpensive endocervical sampling device that minimizes tissue trauma.

(h) To provide an inexpensive endocervical sampling device that prevents inadvertent forward advancement of the brush minimizing premature contact with the brush and the canal, thus, decreasing "false positive" samples.

(i) To provide an inexpensive endocervical sampling device with a tapered distal end which protects the integrity of the brush bristles while resting in the sleeve.

(j) To provide an inexpensive endocervical sampling device that can potentially improve sensitivity of endocervical cell sampling, leading to a more accurate diagnosis of endocervical cancer or pre-cancer.

(k) To provide an inexpensive endocervical sampling device that is disposable.

(l) To provide an inexpensive endocervical sampling device that is efficient, requiring minimal steps to operate.

Briefly described and in accordance with one embodiment, the invention provides an endocervical sampling device and method for efficiently and inexpensively collecting samples of endocervical cells and/or tissue from the walls of the patient's endocervical canal.

Still further objects and advantages will become apparent from a consideration of the ensuing description and drawings.

DRAWING FIGURES

Reference Numerals In Drawings

| | |
|---|---|
| 10 | endocervical sampling device |
| 12 | cytology brush |
| 14 | cylindrical sleeve |
| 16 | tapered tip |
| 18 | penetrable seal |
| 20 | plunger |
| 22 | proximal (operator) end |
| 24 | hub |
| 26 | distal (cervical) end |
| 28 | indicator line |
| 30 | uterine cervix |
| 32 | cervical os (opening) |
| 34 | endocervical canal |
| 36 | proximal sleeve |
| 38 | ectocervix |
| 40 | brush bristles |
| 42 | flange |

DESCRIPTION—FIGS. 1 AND 2A–2C PREFERRED EMBODIMENT

Figure 1:
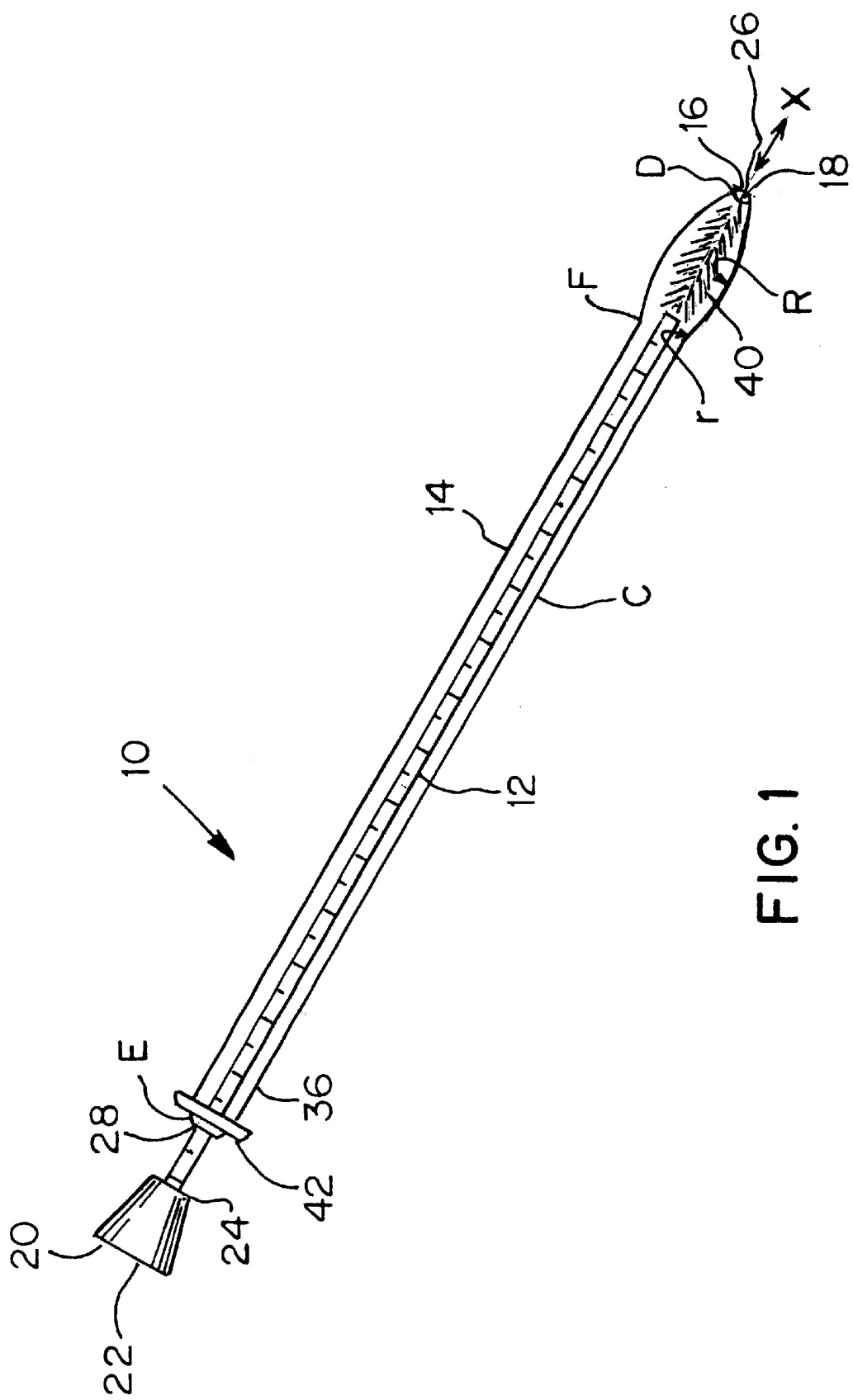
FIG. 1 is a perspective drawing of the preferred embodiment of the present invention.

Referring to the drawings, and in particular to FIG. 1, there is depicted an endocervical sampling device 10, constructed in accordance with the present invention. The endocervical sampling device 10 comprises a cytology brush 12 encased in a protective cylindrical sleeve 14 or sheath 14 which is used for the collection of endocervical tissue and cell samples, particularly with colposcopy. The tapered distal tip 16 has an aperture of sufficient size to accommodate most cervical openings. The tip can be made to any desired opening size to accommodate even very small or stenotic cervical openings. The tip 16 of the device is protected by a penetrable seal 18. The penetrable seal 18 prevents the cytology brush 12 from advancing forward inadvertently. In addition, the penetrable seal 18 on the distal tip 16 softens the edges contacting the endocervical canal 34, thus minimizing tissue trauma. The penetrable seal 18 may be made of plastic, silicone or any suitable material. The cylindrical sleeve 14 is comprised of a rigid or semi-rigid material possibly plastic or other suitable material. The sleeve 14 may be comprised of a non-slip textured or rubberized surface providing a firm grip.

The cytology brush 12 has synthetic bristles 40 at the distal end 26 of a rigid shaft and a plunger 20 /hub 24 combination positioned at the proximal end 22. The plunger 20 is made of a non-slip material or surface to allow ease of manipulation and firmness of grip of the plunger 20. The plunger 20 may be fixed or detachable.

An indicator line 28 is provided on the proximal end 22 to provide visual confirmation of the position of the cytology brush 12 within the endocervical canal 34.

Advantages

From the description above, a number of advantages of my endocervical sampling device become evident:

(a) The protected brush provides superior cell yield while minimizing the risk of "false positive" results, allowing for a more accurate diagnosis of endocervical cancers and pre-cancers.

(b) The use of the tapered tip will obviate the need for the availability of multiple devices to accommodate various cervical opening sizes.

(c) Premature and/or inadvertent canal sampling and specimen contamination is prevented with the use of the protective penetrable seal.

(d) The device can easily and inexpensively be packaged in individual sterile packaging for single use, eliminating risk of infection to patients and health care workers.

(e) The indicator line allows the operator to know at a glance the location of the brush bristles within the sleeve.

(f) The device and method provide the patient with a more comfortable sampling experience.

(g) With my lightweight device and method, the entire sampling procedure can be performed with a minimum of steps even with one available operating hand.

Figure 2A:
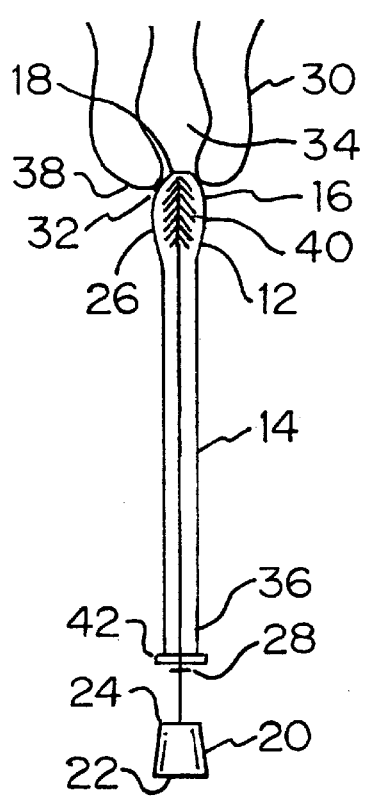
FIGS. 2A through 2C are perspective views of the preferred embodiment of the present invention during use, with the environment of use shown in cross-section.
Figure 2B:
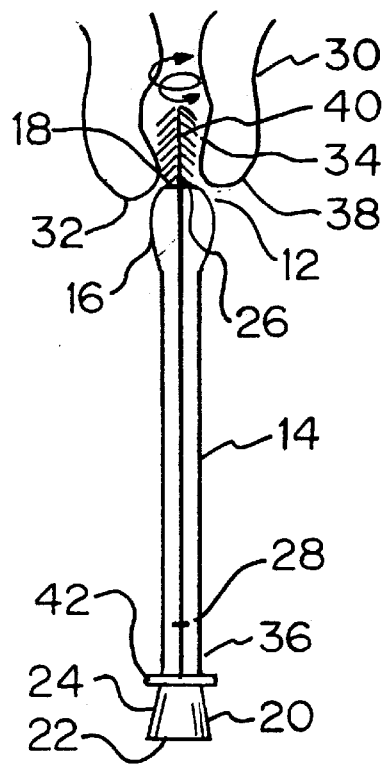
Figure 2C:
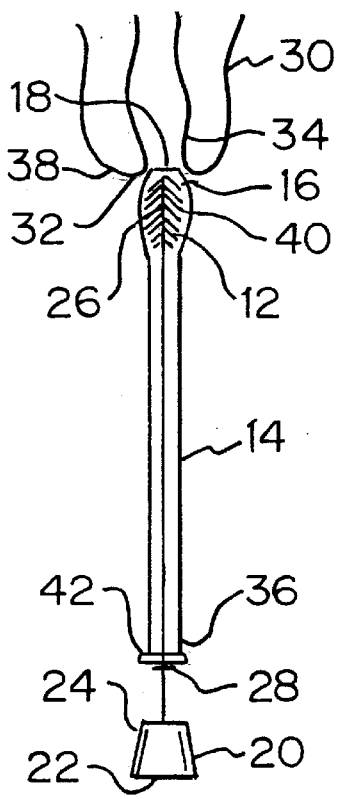

Operation—Referring to FIGS. 2A–2C

The method of utilizing the endocervical sampling device 10 to obtain accurate cytologic or histologic samples in the endocervical canal 34 is as follows:

First, the tapered distal tip 16 is placed at or a few millimeters inside the endocervical canal 34. Determination of the placement depends on proximity of any obvious visualized ectocervical lesions to the cervical os 32. For example, if there is noted a lesion or abnormality just at the opening to the endocervical canal 34, the distal tip 26 of the device should be placed above, or cephalad to the lesion and placed a few millimeters into the canal 34. The plunger 20 is gently pushed at the operator's end 22 penetrating the seal 18, pushing toward the distal end 26 until the hub 24 and the flange 42 abut. This indicates that the cytology brush 12 is in the desired position in the endocervical canal 34. The operator then rotates the brush 12 180 degrees in the canal 34, contacting the walls of the endocervical canal 34 with the brush bristles 40. The operator then manually stabilizes the cylindrical sleeve 14 and withdraws the cytology brush 12 up to the indicator line 28, thus protecting the specimen from contamination from tissue or cell fragments on the ectocervix 38 (face of the cervix), a common problem with brush sampling during colposcopy. The plunger 20 is then advanced distally by applying gentle pressure on the plunger 20. This exposes the brush bristles 40 and the entrapped endocervical cells/tissue for appropriate cytologic or histologic preparation. In general, the bristles are smeared on a glass microscope slide and preserved according to conventional techniques. Alternative preparation is also considered conventional and will not be described herein.

Applicant's invention is an endocervical sampling device that includes a cytology brush slidably received within a sleeve. The cytology brush includes a shaft having a first end and a second end. Bristles are attached to the first end of the shaft and a plunger/hub is attached on the second end of the shaft. An indicator is provided on the shaft between the first end and the second end. A sleeve slidably receives a portion of the brush. The sleeve has a distal end D and a sleeve first end E. The brush shaft and the sleeve extend along the longitudinal axis X. The sleeve has a cylindrical portion C and a tapered tip located at an end F of the cylindrical portion and attached to a cylindrical portion of the sleeve. The tip has a radius r, as measured from the longitudinal axis X, that varies with respect to the longitudinal axis so that initially the tapered tip radius increases to a maximum radius R moving away from the cylindrical portion of the sleeve and then the tapered tip radius decreases at the distal end D of the sleeve. A penetrable seal is attached to the distal end of the sleeve. In operation and in a first position, the bristles are received or contained in the tip and positioned adjacent the seal and the indicator is positioned exterior of the second end of the sleeve. When the plunger is pushed toward the distal end the penetrable seal is broken and the bristles extend outwardly from the sleeve into a second position whereby the bristles extend outwardly from the sleeve and the indicator is positioned within the sleeve.

Conclusion, Ramifications, and Scope

Thus the reader will see that my endocervical sampling device provides an improved, inexpensive, safe, lightweight, comfortable, and efficient means of improving the sample quality of endocervical canal specimens.

It permits the sampling of various sizes of cervical opening with one device.

It can be operated efficiently requiring the dexterity of only one hand.

It provides the superior cell yield of cytology brush sampling of the endocervical canal while minimizing "false positives" associated with that method.

It minimizes the need for curette sampling, promoting patient comfort and eliminating the need to sterilize a metal curette.

It can be manufactured and packaged with inexpensive, even recycled materials in bulk or for single use, minimizing risk of infection.

It provides a method via the tapered tip for protecting the integrity of the brush bristles while resting in the protective sleeve.

It provides a tactile feature (the hub) to allow the operator to know the position of the brush within the canal.

It provides an indicator line providing visual confirmation of the brush position within the protective sleeve.

It provides a soft penetrable seal to improve comfort and the quality of the specimen.

By potentially improving the accuracy of endocervical canal diagnoses, a significant number of unnecessary additional follow up examinations and surgical procedures could be avoided, leading to a decrease in morbidity, mortality and overall cost to society.

Although the description above contains my specificities, these should not be construed as limiting the scope of the invention, but as merely providing illustrations of some of the presently preferred embodiments of this invention. It will, of course, be understood that various modifications and changes in form, detail or method could readily be made without departing from the spirit of the invention. For example, the penetrable seal may vary in material and construction. The tapered tip may be graduated using various shapes and materials, the sleeve may be cylindrical or cone-shaped, and may have various surface textures. The plunger may be otherwise shaped or detachable. The plunger may also be modified in shape or additional features. The indicator line could be various colors. The sleeve may be transparent, opaque or colored. The unit may be made integrally or separately, etc.

Thus, the scope of the invention should be determined by the appended claims and their legal equivalents, rather than by the examples given.

What is claimed is:

1. An endocervical sampling device, comprising:
   a cytology brush having a shaft, said shaft having a first end and a second, bristles attached to said first end of said shaft and a plunger/hub attached on said second end of said shaft and an indicator provided on said shaft between said first end of said shaft and said second end of said shaft;
   a sleeve having a sleeve first end and a distal end, wherein said sleeve slidably receives a portion of said brush, said brush shaft and said sleeve extend along a longitudinal axis, said sleeve having a cylindrical portion and a tapered tip located at an end of said cylindrical portion, wherein a radius as measured from the longitudinal axis of said tapered tip varies with respect to the longitudinal axis so that initially the tapered tip radius increases to a maximum radius moving away from the cylindrical portion of said sleeve and then the tapered tip radius decreases at the distal end of said sleeve; and a penetrable seal attached to the distal end of said sleeve, whereby in a first position said bristles are received in said tapered tip and positioned adjacent said seal, said indicator is positioned exteriorly of said second end of said sleeve and when said plunger is pushed toward said distal end, said penetrable seal is broken and said bristles extends outwardly from said sleeve into a second position and said indicator is positioned within said sleeve.

2. An endocervical sampling device as claimed in claim 1, wherein said sleeve is transparent.

3. An endocervical sampling device as claimed in claim 1, wherein said sleeve is opaque.

4. An endocervical sampling device as claimed in claim 1, wherein said sleeve is colored.

5. An endocervical sampling device as claimed in claim 1, wherein said penetrable seal is made of plastic.

6. An endocervical sampling device as claimed in claim 1, wherein said seal is made of silicone.

7. An endocervical sampling device as claimed in claim 1, wherein said sleeve comprised of plastic.

8. An endocervical sampling device as claimed in claim 1, wherein said sleeve has an outer surface which is textured.

9. An endocervical sampling device as claimed in claim 1, wherein said sleeve has an outer surface which comprises rubber.

* * * * *